US010441336B2

(12) United States Patent
Alleyne (10) Patent No.: US 10,441,336 B2
(45) Date of Patent: Oct. 15, 2019

(54) STABILIZATION OF VERTEBRAL BODIES WITH BONE PARTICLE SLURRY (71) Applicant: Osteoagra LLC, La Jolla, CA (US)

(72) Inventor: Neville Alleyne, La Jolla, CA (US)

(73) Assignee: Osteoagra LLC, La Jolla, CA (US)

(*) Notice: Subject to any disclaimer, the term of this patent is extended or adjusted under 35 U.S.C. 154(b) by 0 days.

(21) Appl. No.: 16/016,635

(22) Filed: Jun. 24, 2018

(65) Prior Publication Data
US 2018/0360513 A1 Dec. 20, 2018

Related U.S. Application Data (63) Continuation-in-part of application No. PCT/US2018/037509, filed on Jun. 14, 2018.
(Continued)

(51) Int. Cl.
A61F 2/28 (2006.01)
A61F 2/30 (2006.01)
A61L 27/54 (2006.01)
A61F 2/44 (2006.01)
A61B 17/88 (2006.01)
A61L 27/58 (2006.01)
A61L 27/36 (2006.01)
(Continued)

(52) U.S. Cl.
CPC ...... A61B 17/8822 (2013.01); A61B 17/8816 (2013.01); A61B 17/8833 (2013.01); A61F 2/2846 (2013.01); A61F 2/30723 (2013.01); A61L 27/025 (2013.01); A61L 27/06 (2013.01); A61L 27/16 (2013.01); A61L 27/365 (2013.01); A61L 27/3608 (2013.01); A61L 27/50 (2013.01); A61L 27/54 (2013.01); A61L 27/58 (2013.01); A61B 2017/8838 (2013.01); A61B 2217/005 (2013.01); A61F 2/44 (2013.01); A61F 2002/2835 (2013.01); A61F 2002/30677 (2013.01); A61F 2310/00359 (2013.01); A61L 2400/06 (2013.01); A61L 2430/38 (2013.01)

(58) Field of Classification Search
CPC ............ A61B 17/8822; A61B 17/8833; A61B 17/8816
See application file for complete search history.

(56) References Cited

U.S. PATENT DOCUMENTS 4,462,394 A * 7/1984 Jacobs ............... A61B 17/8808
606/192
5,472,445 A * 12/1995 Yakimicki .......... A61B 17/8827
366/139
(Continued)

OTHER PUBLICATIONS

International Search Report and Written Opinion dated Sep. 7, 2018 in International Patent Application No. PCT/US2018/037509.
(Continued)

Primary Examiner — David W Bates
(74) Attorney, Agent, or Firm — Veros Legal Solutions, LLP (57) ABSTRACT A medical implant comprises a slurry of bone particles that are injected into a vertebral body under pressure. The liquid component of the slurry may be aspirated while the slurry is being injected so that the bone particles of the slurry pack into the central area of the vertebral body to provide structural support. The injected slurry may be agitated during the procedure to maximize the structural strength of the implant after the procedure.

10 Claims, 4 Drawing Sheets

Related U.S. Application Data (60) Provisional application No. 62/519,409, filed on Jun. 14, 2017.

(51) Int. Cl.
*A61L 27/02* (2006.01)
*A61L 27/06* (2006.01)
*A61L 27/16* (2006.01)
*A61L 27/50* (2006.01)

(56) References Cited

U.S. PATENT DOCUMENTS

| | | | |
|---|---|---|---|
| 5,849,014 A * | 12/1998 | Mastrorio | A61B 17/8808 606/94 |
| 5,989,256 A | 11/1999 | Kuslich et al. | |
| 5,997,580 A * | 12/1999 | Mastrorio | A61F 2/30723 606/95 |
| 6,056,749 A | 5/2000 | Kuslich | |
| 6,217,581 B1 * | 4/2001 | Tolson | A61B 17/8811 606/86 R |
| 6,248,110 B1 * | 6/2001 | Reiley | A61B 10/025 606/192 |
| RE37,479 E | 12/2001 | Kuslich | |
| 6,383,188 B2 | 5/2002 | Kuslich et al. | |
| 6,575,978 B2 | 6/2003 | Peterson et al. | |
| 6,620,162 B2 | 9/2003 | Kuslich et al. | |
| 6,656,185 B2 | 12/2003 | Gleason et al. | |
| 6,695,852 B2 | 2/2004 | Gleason | |
| 6,706,044 B2 | 3/2004 | Kuslich et al. | |
| 6,712,853 B2 | 3/2004 | Kuslich | |
| 7,056,345 B2 | 6/2006 | Kuslich | |
| 7,220,282 B2 | 5/2007 | Kuslich | |
| 7,226,481 B2 | 6/2007 | Kuslich | |
| 7,931,689 B2 | 4/2011 | Hochschuler et al. | |
| 7,959,683 B2 | 6/2011 | Semler et al. | |
| RE42,757 E | 9/2011 | Kuslich et al. | |
| 8,012,211 B2 | 9/2011 | Kuslich | |
| 8,110,212 B2 * | 2/2012 | Marcolongo | A61L 27/52 424/423 |
| 8,690,883 B2 * | 4/2014 | Collins | A61B 17/8811 604/165.01 |
| 8,747,475 B2 | 6/2014 | Kuslich | |
| 8,906,094 B2 * | 12/2014 | Roche | A61B 17/1671 623/17.12 |
| 9,078,884 B2 * | 7/2015 | Lally | A61K 33/42 |
| 9,179,959 B2 * | 11/2015 | Rabiner | A61B 17/7097 |
| 9,387,088 B2 | 7/2016 | Roche et al. | |
| 9,387,277 B2 * | 7/2016 | Buckland | A61L 27/50 |
| 9,526,621 B2 | 12/2016 | Kuslich | |
| 9,550,010 B2 * | 1/2017 | Schulz | A61L 27/12 |
| 9,833,332 B2 * | 12/2017 | Neubardt | A61F 2/4455 |
| 9,844,444 B2 | 12/2017 | Wolfe et al. | |
| 9,913,725 B2 | 3/2018 | Roche et al. | |
| 9,925,058 B2 | 3/2018 | Wolfe et al. | |
| 2002/0147496 A1 * | 10/2002 | Belef | A61F 2/02 623/17.12 |
| 2004/0138703 A1 * | 7/2004 | Alleyne | A61F 2/442 606/213 |
| 2006/0100706 A1 * | 5/2006 | Shadduck | A61B 17/1617 623/17.11 |
| 2006/0122621 A1 * | 6/2006 | Truckai | A61B 17/8811 606/93 |
| 2006/0149268 A1 * | 7/2006 | Truckai | A61B 17/1615 606/79 |
| 2006/0229625 A1 * | 10/2006 | Truckai | A61B 17/1615 606/79 |
| 2007/0093846 A1 * | 4/2007 | Frigg | A61B 17/025 606/90 |
| 2007/0185496 A1 * | 8/2007 | Beckman | A61B 17/8816 606/93 |
| 2008/0033572 A1 | 2/2008 | D'Antonio et al. | |
| 2008/0188945 A1 * | 8/2008 | Boyce | A61B 17/0401 623/23.61 |
| 2009/0098092 A1 * | 4/2009 | Meredith | A61K 35/32 424/93.7 |
| 2010/0076445 A1 * | 3/2010 | Pagano | A61B 17/025 606/94 |
| 2011/0112588 A1 | 5/2011 | Linderman et al. | |
| 2012/0116515 A1 | 5/2012 | Semler et al. | |
| 2012/0245703 A1 * | 9/2012 | Meredith | A61F 2/28 623/23.51 |
| 2012/0265209 A1 * | 10/2012 | Druma | B01F 11/0054 606/93 |
| 2013/0012951 A1 * | 1/2013 | Linderman | A61B 17/1642 606/93 |
| 2014/0257483 A1 * | 9/2014 | Swann | A61F 2/4455 623/17.11 |

OTHER PUBLICATIONS

He, et al. (2015). Bone cements for percutaneous vertebroplasty and balloon kyphoplasty: Current status and future developments. Journal of Orthopaedic Translation. 3. 10.1016/j.jot.2014.11.002.

Wang, et al. Clinical measurement of intravertebral pressure during vertebroplasty and kyphoplasty. Pain Physician. Jul.-Aug. 2013;16(4):E411-8. ISSN 2150-1149.

* cited by examiner

STABILIZATION OF VERTEBRAL BODIES WITH BONE PARTICLE SLURRY

CROSS REFERENCE TO RELATED APPLICATIONS

This application is a continuation-in-part of International Application PCT/US2018/37509, filed on Jun. 14, 2018. This application also claims priority to U.S. Provisional Application No. 62/519,409 filed on Jun. 14, 2017. The entire contents of both the above applications are hereby incorporated by reference.

BACKGROUND

Figures 1, 2:
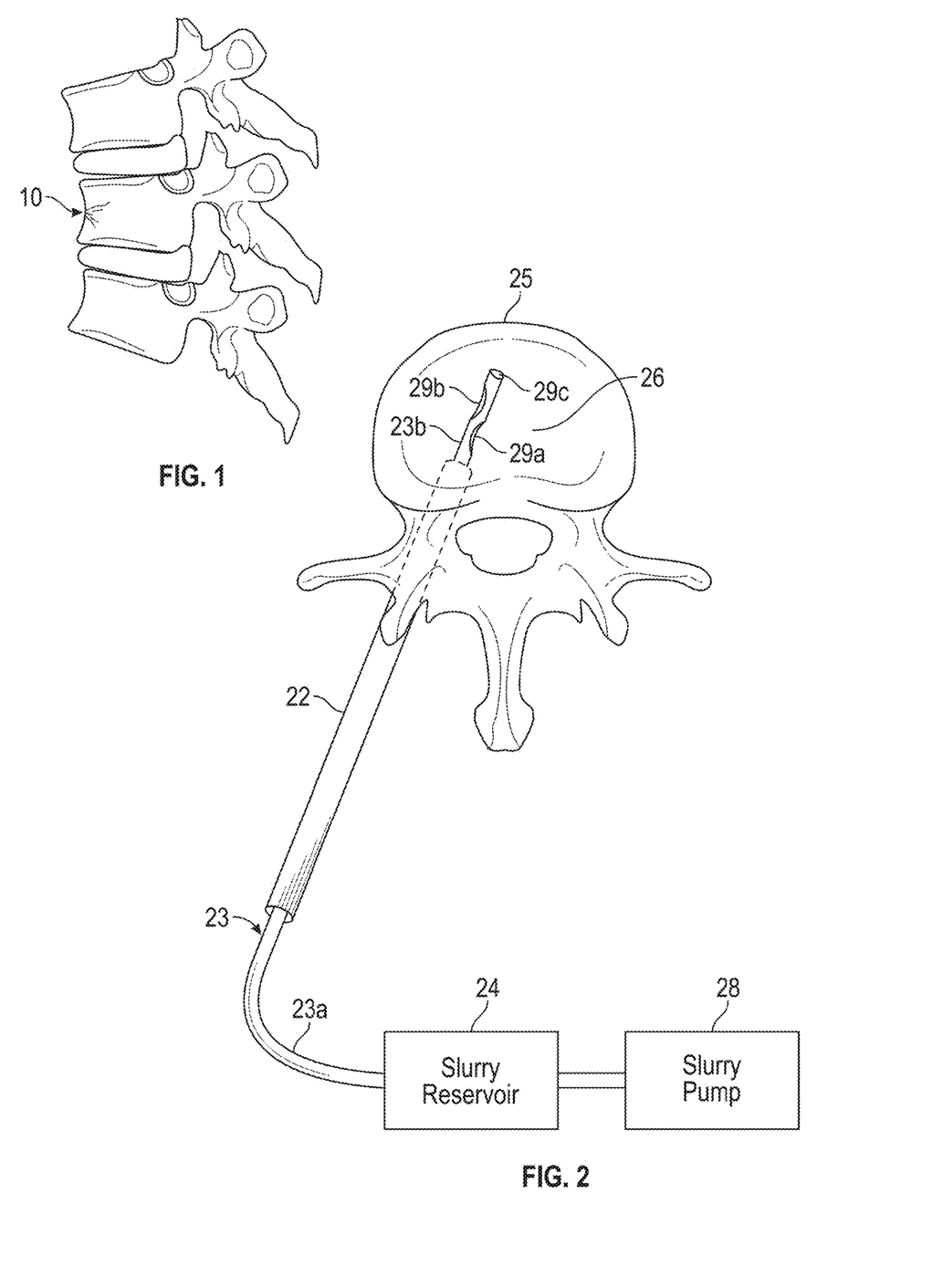
FIG. 1 illustrates a vertebral body with a compression fracture.
FIG. 2 is a schematic block diagram of one implementation of a system in accordance with the present disclosure.

Osteoporosis has continued to be a ubiquitous problem, especially in our elderly population. It is said that osteoporosis sufferers outnumber patients in the United States who have had MI's, stroke, and breast cancer combined. Osteoporosis can result in compression fractures of the vertebral bodies of the spinal column. As shown in FIG. 1, these fractures 10 generally occur in the anterior portion of the vertebra, with this portion compressing to a smaller height than a normal vertebral body. With increasing numbers of osteoporotic compression fractures of the thoracic and lumbar spine, it is felt that 1 in 3 women and 1 in 5 men will have an osteoporotic fracture in their lifetime. By the date 2020, osteoporosis is expected to affect approximately 14 million people in the United States. These fractures become more common obviously in older population and current treatment recommendations include vertebroplasty which can be done as an outpatient and kyphoplasty, which requires an in hospital stay of approximately one day.

PMMA, poly methacrylate, is the substance used in both vertebroplasty and kyphoplasty. This material has been used throughout orthopedics for over 35 years. The first total hip replacements done by Dr. Charnley in Boston and utilized a methacrylate. This material is also known as bone cement and its modulus of elasticity is much higher than that of cancellous or cortical bone. When this material is placed into a vertebral body and is allowed to cure, it creates an exothermic reaction, which can sometimes deaden or destroy nociceptin fibers and once it is hardened, it provides rigid support of the vertebra. Unfortunately, the remaining part of the vertebra and the part in which the cement has been placed cannot grow new bone. The exothermic reaction, if it is close to the endplate, can cause avascular necrosis and result in endplate fracture and adjacent segment collapse. Some of the issues that are associated with the use of PMMA include, but are not limited to, cord compression from ectopic cement extending from the vertebral body into the spinal canal, extrusion of cement through the cartilaginous endplate into the disc, allergic reaction to PMMA, coagulopathy, PMMA getting into the basivertebral sinus resulting in pulmonary emboli and infection because of the foreign body. These are some of the related complications that can occur with vertebroplasty or kyphoplasty. Furthermore, what we have seen over the years is that the cement, which does decrease pain, also appears to cause adjacent segment fractures at a later date. Some as early as a few months and others within a few years. The reason for these compression fractures is: 1) Underlying osteoporosis throughout the vertebral bodies. 2) Cement having a higher density than the cortical or cancellous bone and adjacent microfracturing, which may not have been detected at the time of the initial procedure involving the adjacent vertebra. In addition, compression fractures at T5 or above are technically difficult due to the small pedicle and the parallel orientation of these pedicles. The thoracic spine is also very vulnerable in the event the cement is extruded, which could result in myelopathy or paresis or plegia.

SUMMARY

In one implementation, a surgical kit comprises a cannula configured for accessing the interior portion of a human vertebral body, a catheter having a proximal end and a distal end configured to be inserted into the vertebral body through the cannula, a slurry of bone particles, and a slurry pump configured to force at least some of the slurry of bone particles down the catheter and into the interior portion of the vertebral body. The slurry pump may comprise an inflation syringe. The slurry pump may comprise an auger extruder.

In another implementation, a method of structurally supporting a vertebral body comprises forming one or more openings to a central portion of a vertebral body and placing a cannula through a first opening of the one or more openings. A catheter is inserted into the central portion of the vertebral body through the cannula, and a slurry of bone particles is injected into the vertebral body through the catheter. The slurry is pressurized during and/or after the injecting to force bone particles of the slurry into direct contact with bone tissue inside the vertebral body. After the pressurizing, the catheter and cannula may be removed, and a plug may be inserted into the first opening.

In another implementation, a medical implant for use in structurally supporting vertebral bodies is provided. The implant comprises a slurry of bone particles. Furthermore, the slurry comprises 30% to 85% bone by mass, wherein at least 90% of the bone particles have a characteristic size of 1 micrometer to 1000 micrometers. The bone particles include at least two populations of bone particles having different characteristic sizes, each population comprising at least 10% by mass of the slurry, and wherein the particle size distribution is characterized by a uniformity coefficient D60/D10 of at least 2.

DETAILED DESCRIPTION

General Considerations

In order to be successful in stabilizing these fractures, bone should be inserted, not be a foreign body like PMMA. By inserting cortical allograft or autologous bone particles, we are able to gradually, steadily, increase the bone density within the vertebral body and allow the body to perform its normal healing by not destroying the bone matrix within the vertebral body. PMMA, when it is allowed to cure, creates an exothermic reaction, which then destroys the bone and does not allow bone to incorporate into it. Our material, cortical bone microspheres, allograft or autologous bone will allow the natural healing processes of bone to not only stabilize the fracture, but to heal the fracture with bone. The vertebral bodies receive their blood supply from surrounding tissues and the lumbar spine, lumbar vertebral arteries, the segmental arteries, come off the aorta and supply the blood to the vertebral body to allow it to heal. When PMMA is introduced into a compressed vertebra, yes, it does help to stabilize that vertebra, but in the end, there is no healing that occurs and if the PMMA is very close to the cartilaginous endplate, it may create fractures due to migration of the PMMA or the heat may create osteonecrosis which will then lead to fracturing of the endplate and adjacent segment collapse.

In addition, on complex deformity, correction, in which thoracolumbar or thoracolumbar sacral or thoracolumbar sacroiliac fixation is utilized. The cephalad vertebra can also undergo collapse, kyphosis and fracture. On these long constructs, orthopedic and neurosurgeons have angled the most cephalad screws in a more angled trajectory pointing down at the inferior endplate of the top vertebral body. This angulation of screw is to minimize the forces at the apex and minimize the cut out of these pedicle screws in this very fragile osteoporotic bone for surgical procedures that are complex deformity correction. In addition, some surgeons have extended bone graft above the level of the top screw to minimize fracturing or proximal junctional kyphosis. However, none of these are foolproof because of the diffuse osteopenia or osteoporosis in all of the vertebral bodies. It is therefore contemplated that stabilization above the level of a long construct may prove to be beneficial by inserting PMMA, polymethylmethacrylate, either as a vertebroplasty augmentation or kyphoplasty augmentation. It is our thought process that PMMA will not allow that fracture to heal or that vertebral body to heal. It is purely for stability. Therefore, it is much more prudent to insert these cortical microspheres or cortical cancellous microspheres of autologous or allograft bone into the vertebral body to minimize proximal junctional kyphosis. In addition, this bone graft material can be inserted into the sacrum in order to help increase the bone density in the sacrum or into the ilium or any other bone. Osteoporosis can occur in any bone in the human body. There are 206 bones in the adult of which bones in the foot and ankle are susceptible to fracture and complex open reduction internal fixation is required with bone graft and sometimes methacrylate. In those cases, instead of methacrylate, pressurized microspheres of allograft cortical bone or autologous cortical bone can be used to strengthen the fracture.

Most thoracic and lumbar burst fractures are not treated and matter of fact, is contraindicated for vertebroplasty or kyphoplasty; however, in stable burst fractures our technology by inserting pressurized cortical microspheres of allograft or autologous bone under pressure can be done safely to stabilize burst fractures and minimize the need for surgery. Unstable burst fractures with bone fragments in the canal is still a contraindication even for our technology; however, once the stability has been achieved, the adjacent segments to the fracture, if osteoporotic, can be augmented with our particles of cortical bone whether it be autologous or allograft.

Given the 700,000 to 800,000 vertebral compression fractures that occur each year, the estimated cost for their treatment is anywhere from 13-21 billion dollars per year. The ability to treat these in an effort to allow the natural processes of healing to occur within the vertebral body will allow the vertebral body itself to fill in with bone. Given the blood supply and the compression that exist by placing these particles pressurized through the interstices of the cancellous marrow of the said vertebra, the vertebra may gradually increase its vertebral height and its vertebral bone density. In addition, the vertebral body can be expanded by gradual, steady pressure and be seen under visualization by fluoroscopy, x-ray, CT, ultrasound, MRI. In addition, the particles can, but need not necessarily, be impregnated with a barium compound such as ISOVUE which will allow the vertebral body to be well visualized when the particles are being injected into the vertebra. Moreover, the use of ultrasound to show improved bone density can be performed to look at pre- and post-procedure bone density and vertebral height. With some of the kyphoplasties, early and/or late collapse of the vertebra can occur due to loss of the distraction by the cement or adjacent fracturing of the superior and inferior endplate of said vertebra. With the installation of bone particles, autologous or allograft, we should be able to maintain the vertebral body height and density since bone will attempt to heal within the interstices of the particles.

The present intervention comprises a method and apparatus for spinal stabilization of weak or fractured vertebral bodies or any bone with cortical, autologous or allograft particles via a novel injection apparatus that is capable of measuring pressure and density of the vertebral body. The microspheres can come in a plurality of geometric shapes, that can vary in size or be uniform. The diameter of these microspheres can vary from one micron to 1000 microns diameter, with about 100-200 microns diameter being one specific example size range. In addition, these microspheres can be embedded with barium to allow for better visualization and can vary in the diameter depending on the degree of osteoporosis or collapse. We feel by utilizing incremental impaction bone augmentation through our apparatus, we will be able to deliver significant enough bone material to stabilize the fracture and also increase some of the vertebral height, if not all, as well as allowing the fracture to heal with bone and not allowing the fracture to remain unhealed because of a foreign material, poly methacrylate, in the center or within the vertebral body, which would inhibit in healing.

Example Systems and Methods

Figure 3:
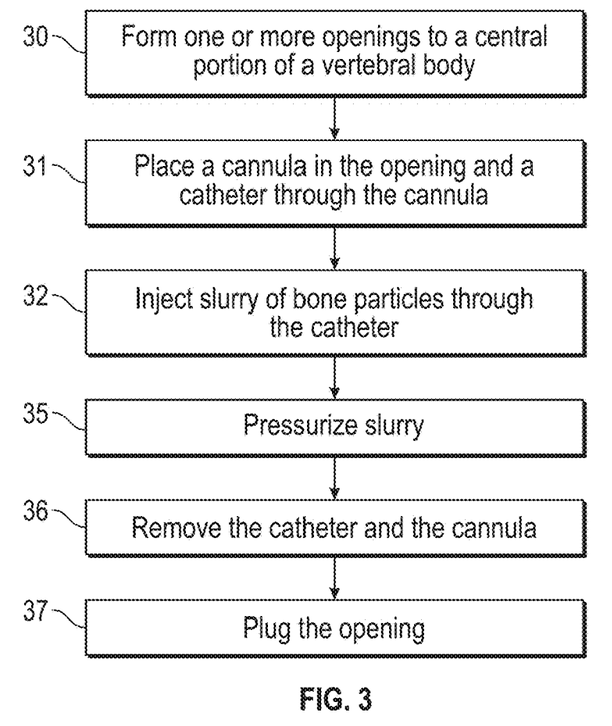
FIG. 3 is a block diagram of a method that may be performed with the system of FIG. 2.

Referring now to FIGS. 2 and 3, one exemplary apparatus and method of vertebral body stabilization will be described. The system of FIG. 2 includes a cannula 22 and a catheter 23 having a proximal end 23*a* and a distal end 23*b*. The cannula 22 is configured for accessing the interior portion of a human vertebral body. The cannula 22 may have an inner diameter in the range of 2.5 to 5 mm, 8 or 10 gauge rigid tubing for example, which is in the range used in conventional vertebroplasty and kyphoplasty procedures. FIG. 2 shows the cannula 22 installed through a transpedicular opening into the interior portion 26 of a vertebral body 25. This is a common location for cannula insertion in currently performed vertebroplasty and kyphoplasty procedures, although a more lateral approach is sometimes utilized. It is also conceived that such a cannula can be inserted through the cartilaginous endplate into the vertebral body.

The catheter 23 is configured to be inserted into the central portion 26 of the vertebral body 25 through the cannula 22 and FIG. 2 illustrates the catheter 23 so positioned. The term catheter as used herein means any form of tube, rigid or flexible, made of any suitable material, whether polymer or metal or both. The catheter may have an inner diameter in the range of 1.5 to 3 mm. At least the distal portion may be formed as a 12, 13, or 14 gauge metal needle for example. The distal end 23b of the catheter 23 includes one or more openings 29a, 29b, 29c. One or more of these openings, such as opening 29a and 29b may be in the side of the catheter to inject material substantially perpendicular to the longitudinal extend of the catheter. An opening 29c may also be provided in the distal tip to inject material parallel with the longitudinal axis of the catheter.

The system of FIG. 2 also includes a slurry reservoir 24. The slurry reservoir 24 contains a slurry of bone particles to be implanted into the inner portion 26 of the vertebral body. A slurry pump 28 may be coupled to the slurry reservoir 24 and catheter 23 to force at least some of the slurry of bone particles down the catheter and into the interior portion 26 of the vertebral body 25. In use, the components of FIG. 2 including the cannula 22, catheter 23, slurry of bone particles 24 and slurry pump 28 may be provided to a physician as part or all of a surgical kit. In such a kit, the slurry reservoir could be made part of the catheter 23 or the slurry pump 28 and be pre-filled with a slurry of bone particles. The volume needed for such a reservoir is the volume of slurry that contains about 5 cc volume of bone particles.

FIG. 3 is a block diagram of a surgical method that can be performed with the apparatus of FIG. 2. At block 30, one or more openings to a central region of a vertebral body are created. This can be done by the same methods that are used in conventional arthroplasty and kyphoplasty procedures such as with a stylet or trocar and/or a bone drill. At block 31, this procedure will leave a cannula behind extending through the opening as shown, for example, in FIG. 2. Also at block 31, a catheter is positioned inside the vertebral body through the cannula. At block 32, a slurry of bone particles is injected into the vertebral body through the catheter. At block 35, the slurry is pressurized. This may occur in conjunction with the injecting of block 32. Pressurizing the slurry can increase the height of the vertebral body as slurry is injected. It is advantageous if this is performed without a bag or other structure enclosing or confining the slurry that is being injected. This can allow direct contact and healing between the implanted bone particles and the bone tissue inside the fractured and/or weakened vertebral body in, for example, a spinal compression fracture, while additionally providing immediate stabilization resulting from the compressed bone particles interlocked in a 'granular mechanic' structure of packed granules resisting further compression or movement and enclosed by the spinal bony fracture fragments and the remainder of the outer shell of the vertebral body.

It is beneficial to monitor the slurry injection under fluoroscopy to visualize the increased density in the vertebral body interior as well as the expansion of the endplates. This may be done without a contrast medium as the accumulation of the denser cortical bone will be visible under fluoroscopy. As explained further below, it is also possible to incorporate a radiopaque contrast medium to the slurry to enhance this visualization.

At the conclusion of the injection, the bone particles will support the vertebral body in its expanded state. Advantageously, this support function can be essentially immediate, similar to a conventional kyphoplasty where the PMMA curing process takes a few hours or even less. After injecting the slurry, the catheter and cannula are removed at block 36. If desired, as shown in block 37, a plug may be placed in the opening that the cannula entered the vertebral body through. Such a plug can be made of a variety of materials including, but not limited to, stainless steel, titanium, cobalt chrome molybdenum, TLA, PGA, PMMA, methylcellulose, or cortical allograft bone.

It may be noted here that the procedure may optionally include the insertion of an inflatable balloon bone tamp prior to injecting slurry. The use of such a bone tamp to create a cavity inside the vertebral body is a familiar part of conventional kyphoplasty procedures.

The slurry of bone particles can take a variety of forms. As used herein, the term "slurry" refers to a flowable mixture of solid particles in a liquid carrier. With respect material content, one suitable slurry composition is bone particles suspended in pure water or saline without any functionally significant additional substances. The slurry may contain 20% to 85% bone by volume. At the lower end of this range, extrusion is more like that of the liquid carrier, and the particles may not interact appreciably in the catheter as the slurry is injected. At the higher end, there will be significant particle to particle contact when the slurry is forced through the catheter. This requires more force to extrude from the catheter, but the material being delivered is closer to its final compacted post-injection form. In some implementations, the slurry may be 40% to 60% bone by volume. Although saline alone can be advantageous, other carriers and/or supplemental substances can be included in some implementations such as blood, platelets, contrast agent, stem cells, and growth factor. Hyaluronic acid can be provided as an extrusion lubricant. As other examples, the particles can be impregnated with biphosphonates, forteo, prolia and fosemax on the surface or as separate substances mixed into the slurry. Other substances such as antibiotics (e.g. vancomycin), chemotherapeutic agents, and the like can also be added to the surface of the particles or as separate substances in the slurry. Particles made of materials other than bone can also form part of the slurry in some implementations.

The bone particles themselves may comprise cortical or cancellous bone, whether allograft, xenograft, or autologous. Cortical bone has favorable compressive strength to perform the desired structural support function. In some implementations, at least 90% of the bone particles are non-demineralized cortical bone particles. Regarding the size distribution of the particles, they can be no larger than the inner diameter of the catheter, and as noted above, may potentially be anywhere in the range of 1 micrometer to 1 millimeter. In some implementations, at least 90% of the bone particles have a characteristic size in the range of 50 to 1000 micrometers. Conceptually, bone particles in this size range may be analogized to grains of sand of varying coarseness. Because the particles may not be entirely spherical, the "characteristic size" of a given particle as defined herein is the diameter of a sphere having a volume equal to that of the actual particle.

A slurry containing substantially uniform particle characteristic sizes in the 50 to 1000 micrometer range may be used, wherein substantially uniform means that the distribution of characteristic sizes (full width at half maximum of a histogram) is within ±10% of the mean characteristic size of the particles in the mixture. Alternatively, the slurry may contain bone particles with two or more different sizes, where two particles are considered to have different sizes if the characteristic size of the larger divided by the characteristic size of the smaller is more than 1.5. Particle size distributions may be characterized by a parameter that may be referred to as the uniformity coefficient. This may be defined as D60/D10, where D60 means 60% of the particles by mass have equal to or smaller characteristic size. Similarly, D10 means that 10% of the particles by mass have equal to or smaller characteristic size. For example, a set of particles half of which (by mass) are 1000 micrometers and the other half (by mass) are 500 micrometers, would have a uniformity coefficient of 2. It can also be seen that a mixture of particles of uniform size would have a uniformity coefficient of 1. Generally, a higher uniformity coefficient corresponds to a greater range of particle characteristic sizes in the particle mixture.

Figure 4:
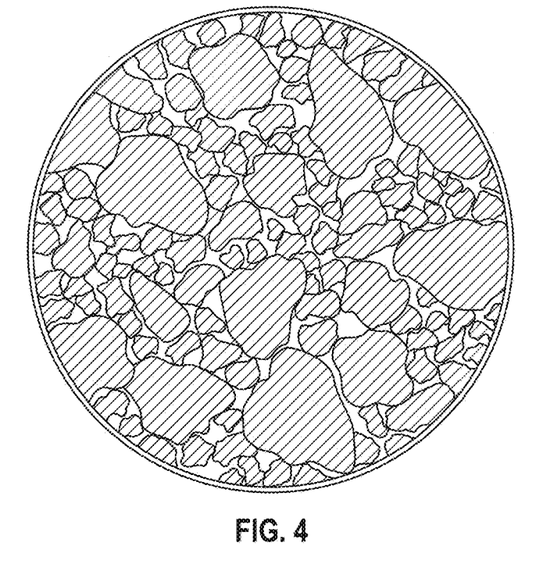
FIG. 4 illustrates a conceptual example of a bone particle size distribution.

FIG. 4 shows a conceptual illustration of a particle distribution that may be suitable for the present application. The example of FIG. 4 may be referred to as "open graded," which generally means that there is a range of particle sizes, but there are few extremely small particles that would substantially fill in the voids between the larger and medium sized particles when they are packed together. In a packed mixture like this, structural support is provided by both the larger particles and the smaller particles. This may be more structurally sound than a substantially uniform particle mixture with fewer points of contact between particles.

In an open graded particle mixture, the open voids may comprise 15% to 25% of the total volume of the packed material. These voids can make the packed bone particle structure water permeable, making it easier and faster for the excess water from the injected slurry to be absorbed or removed as the bone particles pack together on the inside of the vertebral body. These voids also form pores that can be useful for bone ingrowth. Thus, it can be advantageous for the bone particles in the slurry to have a D60/D10 uniformity coefficient of at least 2. In some implementations, the uniformity coefficient is between 2 and 6. In some implementations, the uniformity coefficient is greater than 6. In some implementations, the range of characteristic sizes is limited to reliably produce pores in the packed material such as are shown in FIG. 4. For example, in some implementations, the mean characteristic size of the largest 10% by mass of the particles is no more than 5 times the mean characteristic size of the smallest 10% by mass of the particles.

It is possible to use more complex forms of bone particles as a component of the slurry as well. For example, flexible and compressible spongy webs of bone tissue that may be used as bioscaffolds have been created and are commercially available. Pieces of this type of bone material could be compressed while being injected in the slurry and can expand after exiting to the interior of the vertebral body.

The slurry pump 28 used for delivery of the particle slurry may be similar to a caulking gun or other pressurization device with a knob or trigger or the like to gradually and steadily pressurize the vertebral body with the slurry. The slurry pump may also have a pressure gauge to identify to the surgeon or treating physician how much pressure is being exerted by the slurry pump when performing the slurry injection. The slurry pump 28 should be able to create a pressure at the distal outlet(s) of the catheter inside the vertebral body of about 5-20 psi above ambient atmospheric pressure, similar to the intervertebral pressures that occur in conventional vertebroplasty and kyphoplasty procedures. How much pressure this requires at the proximal end of the catheter near or at the output of the slurry pump 28 will depend on the specific properties of the slurry such as viscosity, as well as the length, lumen diameter, and internal surface characteristics of the catheter. These factors will affect the pressure drop from the input to the output of the catheter. Balloon inflation syringes that are currently used in kyphoplasty procedures that have an output pressure capability of 200 to 700 psi and one of these types of inflation syringes could be used as the slurry pump 28. An electrical rotating auger drive pump could also be used as the slurry pump 28.

Figure 5:
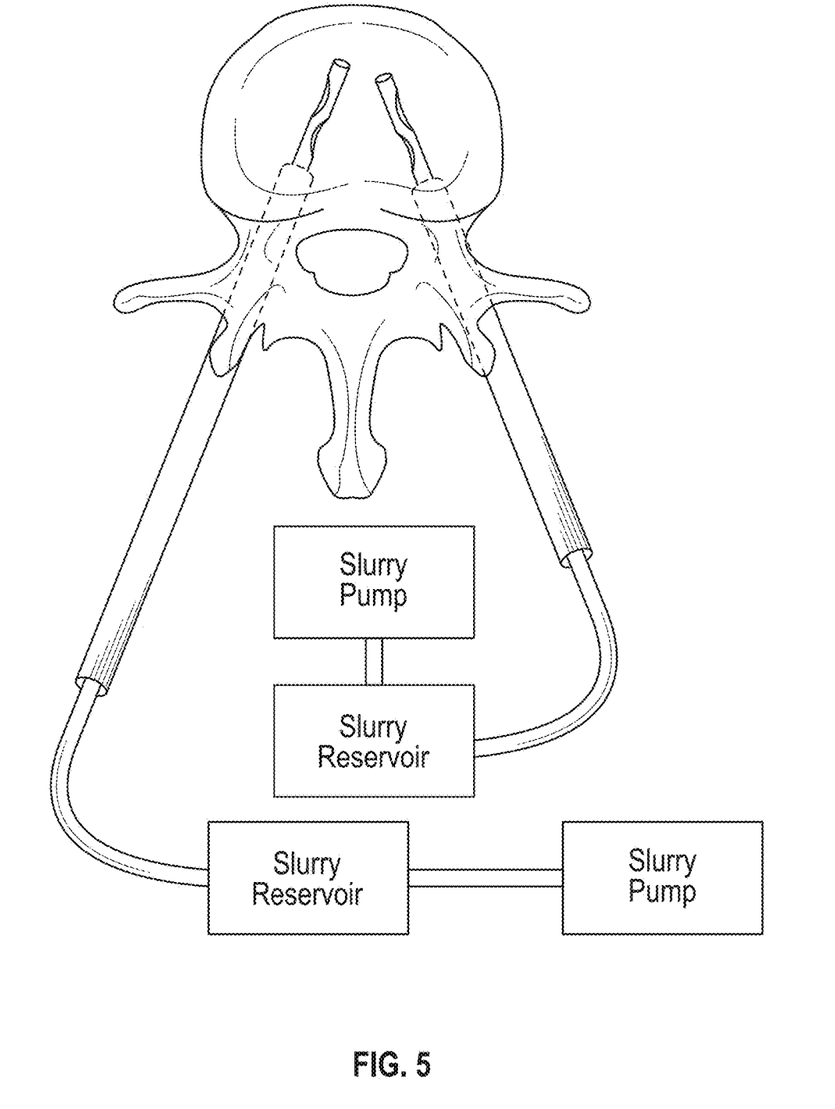
FIG. 5 is a schematic block diagram of another implementation of a system in accordance with the present disclosure including two cannulas and two catheters.

FIG. 5 illustrates a possible bi-pedicular approach, where two openings, two cannulas, and two catheters are used. In this implementation, slurry can be injected into the vertebra at the same time through two catheters. In FIG. 5 two slurry reservoirs and two slurry pumps are also illustrated. This may be convenient for separate monitoring and control of the slurry injection in the two catheters. Also, it distributes the pressurization duty across two separate systems. It will be appreciated, however, that these could be combined into a single reservoir and single pump if desired.

Figure 6:
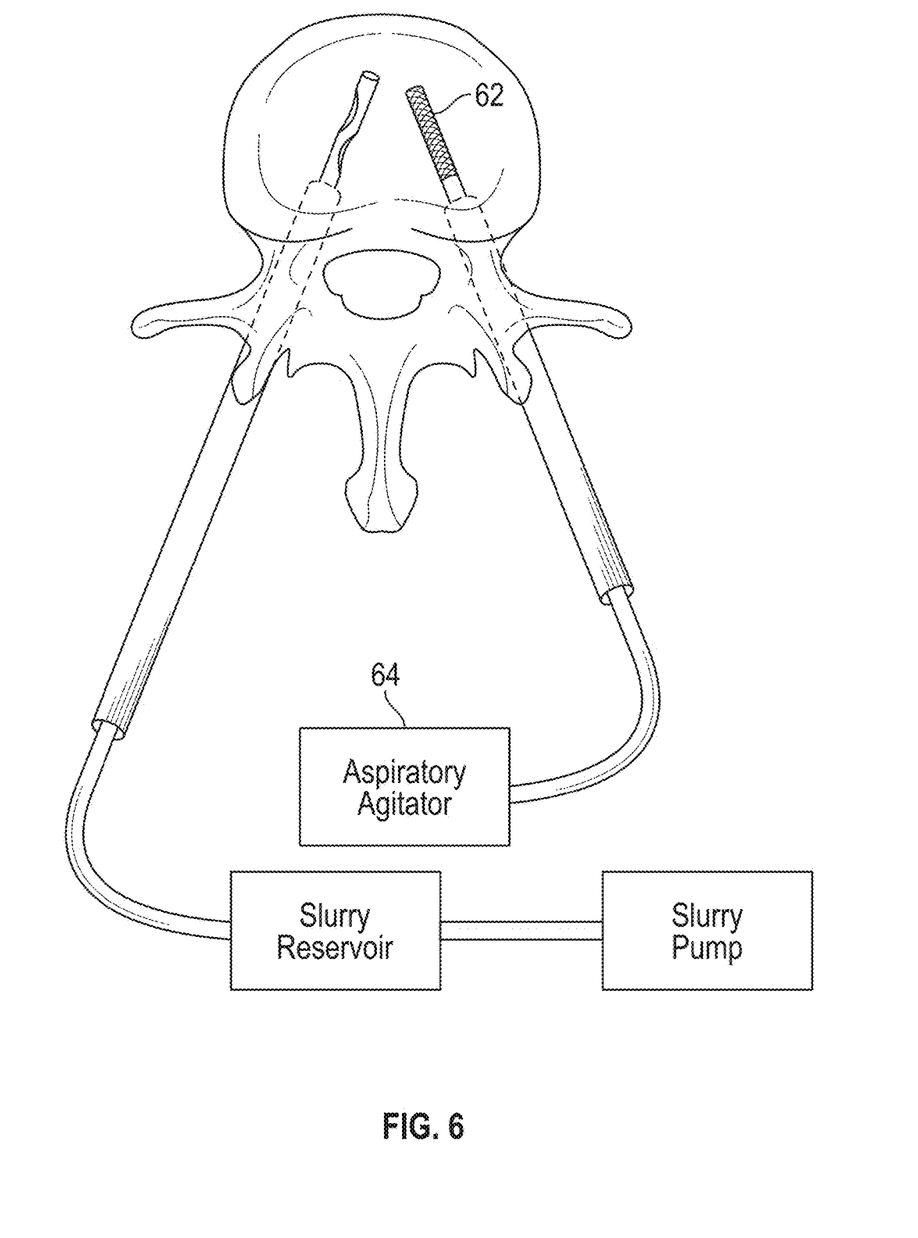
FIG. 6 is a schematic block diagram of another implementation of a system in accordance with the present disclosure including an aspirator.

FIG. 6 illustrates another implementation of the bi-pedicular access also illustrated in FIG. 5. In the implementation of FIG. 6, the second catheter may not be used as another injection pathway for slurry. Instead, the distal end of the second catheter comprises a filtered opening 62. The proximal end of the second catheter is coupled to an aspirator 64 which can be used to aspirate excess slurry liquid as the bone particles of the slurry settle and pack within the vertebral body. Alternatively or additionally, the aspirator 64 can provide an agitation function that can agitate the injected slurry material within the vertebral body as the bone particles of the slurry settle and pack within the vertebral body. This can help ensure that bone particles of different sizes in the slurry remain more homogeneously distributed settle and pack within the vertebral body. To perform agitation and aspiration, the aspirator/agitator may alternate between fluid injection and fluid aspiration. For example, it may inject 0.1 cc, then aspirate 0.2 cc, and so on in rapid succession. The aspiration and agitation functions could also be completely separate. An implantation like this may include reciprocating fins on the second catheter for example. As a further technique for agitation of the slurry as it is injected, the slurry pump 28 could have a mechanism to vibrate or reciprocate the distal end of either or both of the first or second catheters and/or cannulas such as with ultrasound, piezoelectric transducers, or other mechanical means.

Additional Embodiments

The cannula or needle apparatus can also have a distraction device to create a cavity if need be within the vertebral body; however, with gradual pressurization and movement of the needle in multiple directions, the cavitation may not be necessary. Such cavitation if performed, can be done with a spring within the needle sheath to expand the needle in multiple directions or a balloon to expand the fractured vertebra cancellous bone or a cortical cap that can be placed onto the shaft of the needle or cannula that can be used to distract the endplates that have fractured and fill in the bone interstices with our cortical allograft for autologous microspheres. This cortical bone cap may be on the needle or cannula and can be deployed with spring loaded compression to push the endplates back into normal position. This would be the first time that bone would be utilized to distract the compressed vertebra and allow the microspheres to maintain its height and eventually allow the vertebral body to heal. This method of incremental bone impaction can also be utilized at the cephalad or caudal end of a surgical construct such as a posterolateral instrumented fusion to prevent proximal junctional kyphosis or minimize fracture of the sacrum, ileum or lower lumbar spine or any bone.

In the above described specific implementation, there is a separate slurry injection catheter that is inserted into the vertebral body through a cannula placed in the access opening to the inside of the vertebral body. It will be appreciated that it would also be possible to use the cannula directly as an injection and/or aspiration path without using a separate catheter within a cannula, combining the functions of both described above into one element.

In some implementations, the bone particle slurry may additionally contain particles of material other than bone. For example, these non-bone particles incorporated into the bone particle slurry may comprise metal particles such as titanium particles or polymer particles such as PMMA particles, or any mixture of non-bone particles of different types. In some implementations, these non-bone particles may be of relatively small size, such as having a characteristic size of less than 100 micrometers, less than 50 micrometers, or less than 20 micrometers. In these implementations, multiple non-bone particles can become incorporated into the voids illustrated in FIG. 4. In some implementations, such a slurry may be "gap graded" where there are bone particles having a relatively narrow range of large characteristic sizes, and non-bone particles having a relatively narrow range of much smaller characteristic sizes. For example, the mean characteristic size of the smallest 10% of the bone particles in the slurry may be at least five time larger than the mean characteristic size of the largest 10% of the non-bone particles. In these implementations, the non-bone particles can be configured to elute therapeutic substances such as chemotherapy drugs, antibiotics, or the like. Some or all of the non-bone particles may be resorbable. Such a mixture of bone and non-bone particles can provide a desirable combination of structural support with bone material having good compressive modulus properties, and therapeutic support with non-bone material that may easily be made to incorporate therapeutic substances in know manners.

Although the present disclosure has been described in terms of certain preferred features, other features of the disclosure including variations in dimensions, configuration and materials will be apparent to those of skill in the art in view of the disclosure herein. In addition, all features detailed in connection with any one aspect herein can be readily adapted for use in other aspects herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

What is claimed is:

1. A method of structurally supporting a vertebral body comprising:
   forming one or more openings to a central portion of a vertebral body and placing a cannula through a first opening of the one or more openings;
   injecting a slurry of bone particles through the cannula, wherein the slurry of bone particles consists essentially of bone particles, water, and optionally one or more additional ingredients selected from salts, growth factor, blood, platelets, contrast agent, stem cells, antibiotics, chemotherapeutic agents, bisphosphonates, and osteoporosis therapy drugs,
   pressurizing the slurry during and/or after the injecting to force bone particles of the slurry into direct contact with bone tissue inside the vertebral body.

2. The method of claim 1 comprising:
   inserting a catheter into the central portion of the vertebral body through the cannula;
   injecting the slurry of bone particles through the catheter.

3. The method of claim 1 comprising:
   removing the cannula; and
   inserting a plug into the first opening.

4. The method of claim 1, comprising aspirating liquid from the central portion of the vertebral body.

5. The method of claim 1, comprising agitating the slurry in the vertebral body during the injecting.

6. The method of claim 1, comprising forming at least a second opening to the central portion of the vertebral body.

7. The method of claim 6, comprising
   placing a second cannula through the second opening of the one or more openings;
   injecting a slurry of bone particles through the second cannula at the same time as injecting a slurry of bone particles through the first cannula.

8. The method of claim 6, comprising:
   placing a second cannula through the second opening of the one or more openings;
   aspirating liquid from the central portion of the vertebral body through the second cannula while injecting the slurry of bone particles through the first cannula.

9. A method of structurally supporting a vertebral body comprising:
   forming one or more openings to a central portion of a vertebral body and placing a cannula through a first opening of the one or more openings;
   injecting a slurry of bone particles through the cannula, wherein the slurry of bone particles is 20 to 85 percent bone by volume, and
   pressurizing the slurry during and/or after the injecting to force bone particles of the slurry into direct contact with bone tissue inside the vertebral body.

10. The method of claim 9, wherein at least 90% of the bone particles are non-demineralized cortical bone particles.

* * * * *